United States Patent [19]

Goshgarian

[11] Patent Number: 4,592,725
[45] Date of Patent: Jun. 3, 1986

[54] ORTHODONTIC PALATAL ARCH BAR AND METHOD OF USING SAME

[76] Inventor: Robert A. Goshgarian, 1071 Ash Lawn, Lake Forest, Ill. 60045

[21] Appl. No.: 728,274

[22] Filed: Apr. 29, 1985

[51] Int. Cl.⁴ ............................................. A61C 7/00
[52] U.S. Cl. ........................................ 433/7; 433/24
[58] Field of Search ................................ 433/7, 24

[56] References Cited

U.S. PATENT DOCUMENTS

| | | | |
|---|---|---|---|
| 3,162,948 | 12/1964 | Gerber | 32/14 |
| 3,256,602 | 6/1966 | Broussard et al. | 32/14 |
| 3,792,529 | 2/1974 | Goshgarian | 433/7 |

Primary Examiner—Robert Peshock
Attorney, Agent, or Firm—McWilliams, Mann, Zummer and Sweeney

[57] ABSTRACT

A palatal arch bar of the removable and adjustable palatal arch wire type disclosed in Goshgarian U.S. Pat. No. 3,792,529 which is improved to have a dual upper arch usage, whereby the arch bar may be applied from the mesial and used as disclosed in said patent to derotate the first permanent molars, and then removed, reversed and reapplied to the molars from the distal to use them as anchor molars in the translation of the upper arch canines. The improved arch bar comprises an arch wire equipped with a fitting or spur adjacent each terminal end of the arch wire that adapts the arch bar for use in bodily retraction of the maxillary permanent canine teeth. The spurs of the arch wire are each located on the arch wire to be disposed at the level of the centrum of the respective maxillary first permanent molars when the arch wire is arched by the orthodontist in shaping it for application to a particular patient, and are disposed to be anteriorly directed, and thus inoperative, when the arch wire is applied as disclosed in said patent. In the second use of the arch bar, after the arch bar is removed, and pivoted 180 degrees, and re-applied to the maxillary first molars from the distal, with the spurs forming now being positioned to be each connected, by a lingual elastic, to a canine mounted lingual hook on the same side of the jaw as the molar, with the canine mounted hook being disposed at the level of the centrum of the canine in question.

16 Claims, 11 Drawing Figures

ORTHODONTIC PALATAL ARCH BAR AND METHOD OF USING SAME

This invention relates to devices or implements and methods of using same in the practice of orthodontics on the upper arch, and more particularly to improvements in the orthodontic arch bar disclosed in the Applicant's prior U.S. Pat. No. 3,792,529, granted Feb. 19, 1974, which improved arch bar is arranged to facilitate the repositioning of maxillary teeth other than, and in addition to the upper arch first permanent molars, and specifically facilitate the repositioning and straightening of the permanent canines.

Orthodontics is a specialty of dentistry dealing with the correction of positional irregularities of the teeth. The practice of this specialty involves the patient undergoing a series of procedures that require many months to complete.

These procedures involved a period of active treatment, during which positionally displaced teeth will be physically shifted, this usually heretofore having been accomplished by the attachment of dimensionally slotted brackets to the permanent teeth, with biasing, so called "arch" wires of appropriate cross section and outline, which have been bent to a predetermined form, being inserted into the brackets in question and secured in place. The arch wires involved are configured and applied to transmit to the attachments to the teeth predetermined forces that act on the teeth to either tip them, rotate them, or bodily carry the teeth, to predetermined positions that will dispose the teeth (whose positions are being corrected) in alignment with the normal arch or curve defined by the patient's jaw.

My above identified U.S. Pat. No. 3,792,529 is directed to a palatal arch bar that is specifically adapted for reciprocable application to the patient's maxillary first permanent molars for derotating, expanding, contracting, intruding and/or torquing same in order to provide a mechanically improved relationship in contact with corresponding molars of the opposing or mandibular arch, as well as to increase the space to facilitate and improve the alignment and relationship of the remaining teeth. The arch bar of my said prior patent comprises an arch wire that has its end portions formed to fit into lingually projecting brackets that are respectively suitably affixed to metal bands or sheaths applied on the maxillary first molars, and from the mesial. This patented arch wire is characterized by an intergal U shaped open loop portion intermediate its ends, the legs of which can readily be brought together or spaced apart by the orthodontist in order to incorporate lesser or greater reciprocable force on the maxillary first molars, to both of which the patented arch wire is removably applied. The patented arch wire is readily applied to and removed from the patient's mouth, and has been particularly useful in the initial orthodontic procedures employed by the orthodontist in treating the patient's upper arch to properly position the maxillary first permanent molars and thereby reduce the crowding of the upper arch anterior teeth to adjust to the proper occlusion and bite, and to increase the anchorage in expediting the straightening of the patient's teeth.

The arch bar of my said patent provides the important advantage that the arch wire open loop may be readily adjusted by the orthodontist, by either opening it or compressing it, to provide the biasing forces desired, depending upon the orthodontist's analysis of the rotational, tipping, and torquing to augment the anchorage requirements of the particular patient and his maxillary first permanent molars.

However, the arch bar of the Applicant's said patent, after the maxillary first permanent molars have been positioned as desired, has no further utility in the tooth straightening procedure, other than being employed in a passive condition to maintain the indicated first permanent molars in their desired positions of repositioning.

A major objective of the Applicant's present invention is to provide a revised arch bar that provides the functions of the arch bar disclosed in the Applicant's said patent, and is also useful in treating the patient's maxillary teeth that are anterior of the first permanent molars.

The Applicant's work in the field of orthodontics has revealed to him that in the mechanics involved in straightening the maxillary arch, the palatal root of the maxillary first permanent molars should be involved in the straightening of the maxillary teeth anterior to same because the first permanent molar palatal root is the most massive of its roots, and it has occurred to the Applicant that it would present a mechanical advantage to use this first permanent molar palatal root as part of the anchorage system in applying forces to the canines and maxillary anterior teeth to reposition same as part of the orthodontry work being done on a particular patient.

The Applicant has also determined that it is important that the forces delivered by the arch wire and applied to the canines should be effective, for best results, at the centrums of the maxillary first permanent molars and canines. In this connection, the term "centrum" as employed in this disclosure and the appended claims means the point of intersection of the axis of rotation of the tooth about its longitudinal center, and the tipping axis of the tooth as the result of torquing such teeth to a more desirable position.

Accordingly, it is a principal object of the present invention to improve the arch bar of the Applicant's said patent, by providing fittings or spurs on same that are inoperative when the arch bar is positioned and used as disclosed in said patent, in connection with the maxillary first permanent molars, but which fittings are rendered operative by removing, repositioning, and reapplying the improved arch bar, and by employing the use of a lingual hook on the lingual aspect of each canine, and a lingual elastic applied between the arch wire fitting and canine mounted hook on the respective sides of the maxillary arch involved, that enables the force system to be applied to the patient's upper jaw using conventional labial elastics optionally and/or labial located arch wires, or face bows (if necessary), to generate a constant distalizing and torquing action on the anterior teeth that results in the maxillary teeth anterior of the first permanent molars being properly oriented and aligned to present the desired result of straight teeth with good occlusion.

Another principal object of the invention is to improve the practice of orthodontics of the upper arch by the provision of a modified and improved arch bar, over that disclosed in the Applicant's said prior patent, that in the mesial applied position of the arch bar, the treatment of the maxillary first permanent molars as to rotating, expanding, contracting, intruding and/or torquing, may first be effected as disclosed in said patent, after which the modified and improved arch bar is removed, pivoted 180 degrees, and reapplied to the maxillary first molars from the distal, to permit the treated maxillary first permanent molars to be used as anchor molars in the orthodontic procedure that is to follow, and to provide for proper biasing of, specifically, the maxillary permanent canine teeth, during the subsequent teeth straightening procedures.

Yet another principal object of the invention is to provide improved methods of treating the maxillary first permanent molars and permanent canine teeth that simplifies and makes more certain the practice of orthodontics on patients, and enables the patient to contribute to expedited results, as by daily changing of easily reached lingual elastics that are employed in accordance with the invention, where this is feasible in the treatment of the patient's particular upper dental arch condition.

In accordance with the invention, an orthodontic arch bar type appliance for application to the patient's dental upper arch is provided comprising a length of spring steel wire adapted for application across the upper arch palate and between the first permanent molars of the upper arch, which thus may be designated the anchor molars of this invention; the improved arch wire defines a pair of spaced oppositely extending body portions integral at like ends with a centrally located, open U-shaped, spring loop, adjacent the mid portion of the arch wire that projects laterally of the bar and has its loop leg portions coplanar related, with the wire body portions at their respective other ends being doubled over and disposed normally of the respective body portions in substantial coplanar relation to project from the arch wire in substantially the same direction as the loop and form the arch wire terminal end portions. The indicated open loop is the adjustable open loop of the arch wire of my said prior patent.

As part of the orthodontics practice in accordance with the invention, metal bands or sheathes are first applied to each of the maxillary first molars, which bands or sheathes are each provided with, on their lingual aspects, lingually projecting brackets that each define a quadrilaterally configured mesiodistally oriented, through opening, with the respective arch wire terminal end portions being resiliently received in the respective bracket through openings after the arch wire has been suitably arched by the orthodontist in conformance with the patient's upper arch palate transversely thereof so as to span the distance between the lingual aspects of the respective maxillary first permanent molars.

The arch wire body portions, in accordance with the present invention, are each provided with a fitting or spur that is located or spaced from the respective arch wire terminal end portions to be disposed at the level of the centrum of the maxillary first permanent molar adjacent it, when the arch wire has been arched and operatively applied to and between the maxillary first permanent molars. The indicated fitting or spurs are disposed to substantially parallel the arch wire terminal end portions and project oppositely of same, with the spurs of fittings being oriented such that when the arch wire is applied from the mesial to act on the first permanent molars in accordance with the Applicant's said prior patent, the fittings or spurs provided by the improved arch bar are inoperative.

However, after the procedures pertaining to the maxillary first permanent molars specified by the Applicant's said patent have been performed, the improved arch bar may be removed, pivoted or swung end for end 180 degrees, and reapplied from the distal, to the same molar bracket through openings, to dispose the indicated spurs or fittings in their operative positions.

In addition, at the convenience of the orthodontist, whether prior to use of the arch wire in accordance with the Applicant's said prior patent, or after such use in connection with the needed repositioning of the maxillary first molars, each maxillary canine tooth has applied to its lingual aspect a lingual hook that is directed to the gingival, and is to provide an elastic band connection to the canine at the level of the centrum of the canine tooth involved.

With the improved arch bar of this application reapplied as indicated, the arch wire spurs or fittings are directed to the distal, and one of these spurs accepts a first lingual elastic at one end of the latter, with the other end of the elastic being applied to the lingually oriented hook of the maxillary canine tooth on that side of the arch. On the other side of the arch, a similar lingual elastic is applied to the arch bar spur on that side of the arch as well as to the lingually oriented canine hook on the same side of the arch. The result is that the maxillary first permanent molars serve as anchor molars in biasing the canines to have a distobuccal rotational effect, with the canines also having applied to them a root distalizing force. Additional horizontal moments are applied to the maxillary teeth anterior to the first permanent molars by employing conventional orthodontic appliances such as labial elastics, labial arch wires, face bows, or the like, to generate a force system on the upper arch (as determined to be needed by the orthodontist) that restores the teeth of the upper arch in the manner that is the objective of good orthodontic practice.

The invention also contemplates the provision of improved methods of procedure of practicing orthodontics that are provided by the herein disclosed use of the Applicant's improved arch bar, both with and without requiring extraction of maxillary teeth (such as the first bicuspids), to anchor the arch wire and bias the canines, as needed for straightening the teeth, of the upper dental arch with good occlusion results.

Still other objects, uses and advantages will be obvious or become apparent from a consideration of the following detailed description and the application drawings in which like reference numerals indicate like parts throughout the several views.

In the drawings:

FIG. 4 is an inferior plan view of a patient's upper dental arch, showing the arch bar of FIG. 3 applied thereto in the manner contemplated by the Applicant's said prior patent, for use in repositioning the patient's maxillary first permanent molars in one or more of the manners disclosed in said patent (this being the application of the improved arch wire involved to the upper arch from the mesial), with the view of FIG. 4 also depicting the case where the first bicuspids of the patient's upper dental arch have been removed to provide room for placing displaced upper arch anterior teeth (that remain) in their properly aligned relation in the arch, and illustrating the feature of the invention, that the upper arch permanent canines have each had applied thereto at their lingual aspects the gingival directed lingual elastic attachment hooks that are not used in the mesial applied arch bar condition of FIG. 4;

However, it is to be distinctly understood that the specific drawing illustrations provided have been supplied primarily to comply with the requirements of the Patent Laws, and that the invention is susceptible of other embodiments and procedures that will be readily apparent to those skilled in the art, which are intended to be covered by the appended claims.

Figures 1, 2:
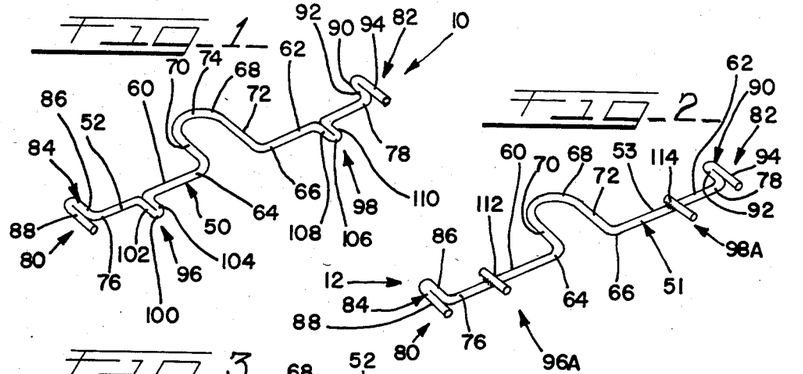
FIG. 1 is a large scale perspective view of the improved arch bar, showing one embodiment of the improved arch bar prior to the arch wire involved being arched by the orthodontist for application to a particular patient.
FIG. 2 is similar to that of FIG. 1, but illustrates a modified form of arch bar in accordance with the invention.

Reference numeral 10 of FIGS. 1 and 3-10 indicates a preferred form of the improved arch bar, while reference numeral 12 of FIG. 2 illustrates a modified form of arch bar in accordance with the present invention that is adapted for the same application shown in FIGS. 4-10.

Figure 3:
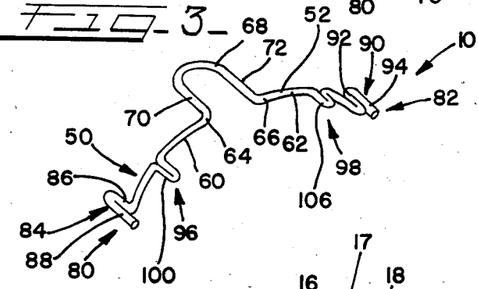
FIG. 3 is a view similar to that of FIG. 1, showing the arch bar of FIG. 1 arched for application to a patient's upper arch from the mesial, such as the arch shown in FIG. 4.
Figure 4:
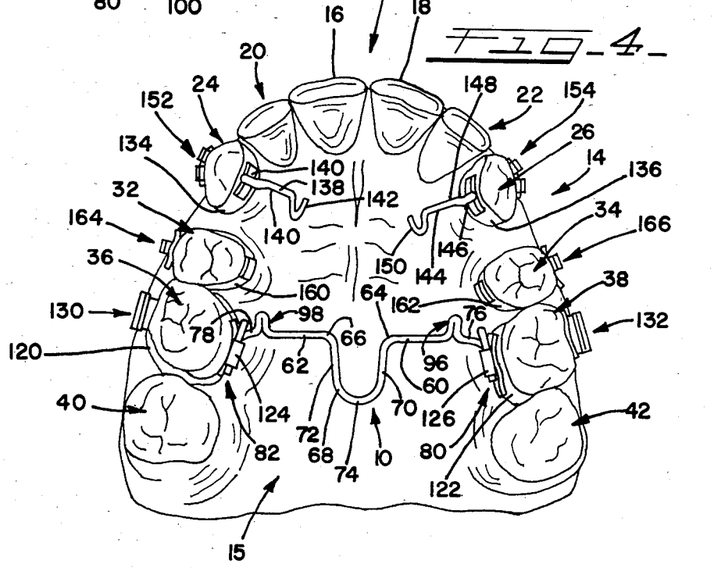
Figure 5:
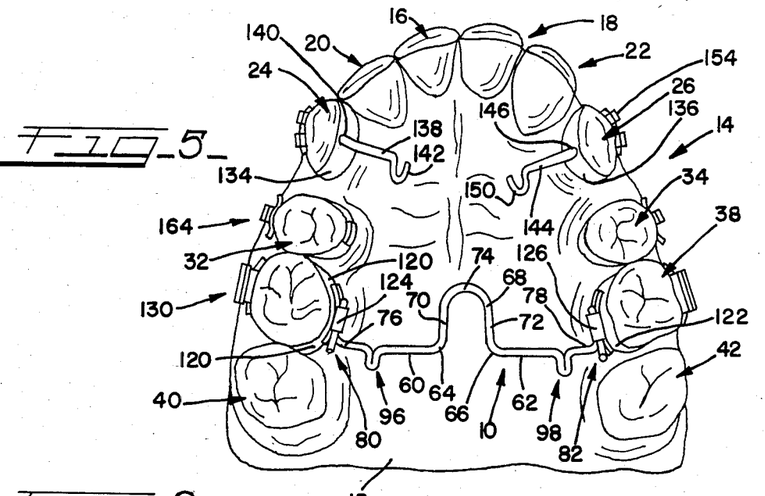
FIG. 5 is a view similar to that of FIG. 4, but showing the improved arch bar after it has been removed from the position of FIG. 4, pivoted 180 degrees, and reapplied to the patient's maxillary first permanent molars from the distal, thus rendering the spurs or fittings of the arch bar operative for connection to the illustrated canine lingually and gingivally oriented attachment hooks in accordance with the invention.
Figure 7:
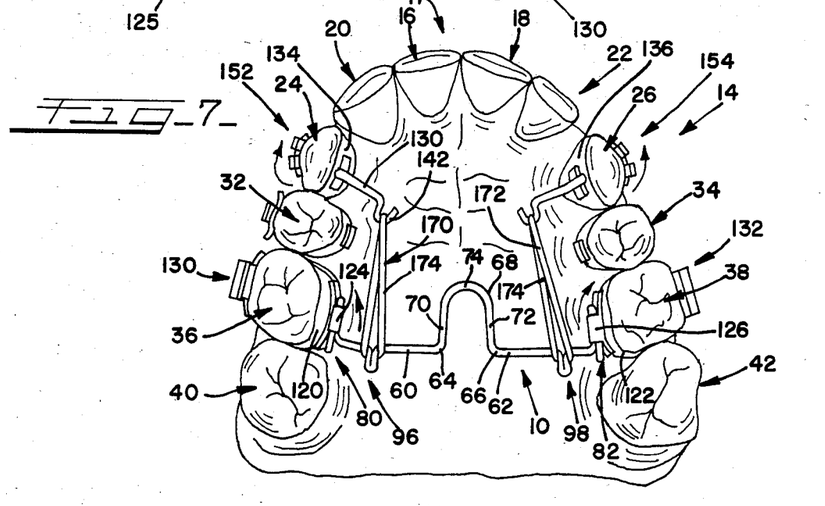
FIG. 7 is a view similar to that of FIG. 5 showing the arch bar and canine lingual hook application of FIG. 5. illustrating also the pair of lingual elastics that are applied on either side of the upper arch, with one of the elastics being applied between one of the arch wire spurs and the canine lingually oriented hook on that side of the arch, and the other lingual elastic being applied between the spur at the other side of the arch and the canine lingually oriented hook on that side of the arch, with the arrows adjacent the canines indicating the resulting canine rotational movement biasing action involved as the result of the application of the lingual elastics at either side of the upper jaw.

In the diagrammatic showings of FIGS. 4, 5 and 7, the upper arch inferior plan view of a patient is diagrammatically illustrated showing in sequence the application and use of the preferred form of arch bar shown in FIGS. 1 and 3, with the upper jaw being generally indicated by reference numeral 14, and illustrating the central incisor teeth at 16 and 18, the lateral incisors 20 and 22, the canine teeth at 24 and 26, the second bicuspids at 32 and 34, the first molars at 36 and 38, and the second molars at 40 and 42.

The specific procedure described in the disclosure and the orthodontic methods involved in employing same, contemplate that the first bicuspids have been removed or extracted to provide additional space for straightening or realigning the remaining teeth of the upper jaw in its arch, the bicuspids of the lower jaw or mandibular teeth are also assumed to be removed for similar purposes. However, the the teachings of the present invention are applicable whether or not tooth extraction is preformed, since where adequate space in the arch is available for the orthodontist to perform his teeth straightening task, the principles of the present invention are fully applicable without extraction, as will be plainly apparent to those skilled in the art.

In accordance with the invention, the arch bar 10 of the present invention comprises an arch wire 50, bent in the form of FIGS. 1 and 3 - 1 which is of one piece construction, and is in the form of a length 52 of a suitable filamentous, resiliently flexible material, such as or comparable to stainless steel wire, which in the preferred form is 0.036 inch in diameter; however, it is to be understood that other materials and diameter sizes could be utilized for the purposes of this invention, and the invention is by no means to be limited or confined in this respect. The arch bar 12 comprises an arch wire 51 in the form of length 53 of wire that is the same as that of arch wire 50, but the arch wire 51 is not of one piece construction, as indicated in FIG. 2.

The indicated stainless steel wire forming wires 50 and 51 has an inherent spring like resiliency, the importance of which quality will become apparent as the disclosure proceeds. The arch wire 50 and the arch wire 51 are formed from wire lengths of varying dimensions to fit each particular patient's dental arch, as determined by the measurement in millimeters made by the orthodontist between the upper arch first molars 36 and 38, across the palate 15 represented by the upper jaw 14.

For most purposes, for example, four different wire lengths, such as 34 millimeters, 37 millimeters, 41 millimeters, and 45 millimeters, will provide adequate variety to accommodate the majority of patients. Again, however, the lengths of the wire employed to form the respective arch bars 10 and 12 is not a critical feature of the present invention, and the invention is by no means to be limited in this respect.

The preferred arch wire 50 comprises the wire length 52 being formed to define a pair of spaced oppositely extending body portions 60 and 62 that are integral at like ends 64 and 66 with an open U-shaped spring loop 68 that projects laterally of the bar 10 and is defined by substantially parallel leg portions 70 and 72 which are integral with the generally semicircular mid portion 74, with the open loop portion 68 having its leg portion 70 and 72 substantially coplanar related in the indicated parallel relation, in the preapplication form of FIG. 1.

The arch wire body portion 60 and 62 at the respective other ends 76 and 78 define terminal end portions 80 and 82, respectively, that project laterally of the arch bar 10 and are in substantial parallelism with the legs 70 and 72 of the open loop 68, in the preapplication form of FIG. 1. As indicated in the drawings, the arch wire body portions 60 and 62 extend generally normally of the open loop leg portions 70 and 72 and the respective terminal end portions 80 and 82.

The terminal end portions 80 and 82 are similar in configuration, the end portion 80 comprising a doubled over segment 84 of the wire 52 involving substantially abutting lengths 86 and 88 that give the terminal end portion 80 the rectilinear elongate configuration that is effectively quardilateral in cross section when the arch bar 10 is shaped in the manner shown in FIG. 3 for application as hereinafter described.

The terminal end portion 82 similarly comprises a doubled over segment 90 of the wire 52 comprising wire portions 92 and 94 that have the similar shaping referred to in connection with the description of the terminal end portion 80.

The arch bar 10, and specifically its respective body portions 60 and 62, has a first spur or fitting 96 formed in the body portion 60 and a second spur or fitting 98 formed in the body portion 62. The spur or fitting 96 comprises a doubled over segment 100 of the wire 52 comprising wire sections 102 and 104, while the spur or fitting 98 comprises similarly doubled over wire segment 106 comprising wire sections 108 and 110. Spurs or fittings 96 and 98 preferably have a similar length, laterally of wire 52 that approximates three to four millimeters, though again this length is not a critical feature, and the invention is by no means to be limited in this respect.

The arch bar 12 comprises the arch wire 51 formed by wire length 53 to define the body portions 60 and 62, open loop 68, and the terminal end portions 80 and 82, as indicated by corresponding reference numerals to the corresponding parts of FIG. 1. However, the spurs or fittings 96A and 98A of the arch bar 12, instead of being in the form of the doubled over wire segments that are indicated in the showing of FIG. 1, comprise separate wire elements 112 and 114 affixed to the respective body portions 60 and 62 as by employing a suitable bonding of the wire segments 112 and 114 to wire 55, using silver solder or the like. Wire elements 112 and 114 are preferably formed from the same size stainless steel wire as wire length 53, and are affixed to wire length 53 at like ends of same to project laterally of the respective body portions 60 and 62 in the same manner and to the same extent as segments 100 and 106 of arch bar 10.

It is a feature of the invention that the spurs or fittings 96, 98, and 96A and 98A, are oriented to project at right angles to the respective arch wire body portions 60 and 62, and be in substantial parallelism while projecting oppositely of the open loop portion 68 and the terminal end portions 80 and 82, or the respective arch bars 10 and 12 as indicated in the drawings. As will be clear from the disclosure as it proceeds, it is intended that in one manner of use or application of the arch bars 10 and 12, the spurs or fittings 96, 98, 96A and 98A, are inoperative, but in the reverse position of the respective arch bars 10 and 12, they are operative in the manner indicated in FIG. 7.

In FIG. 3, the arch bar 10 is shown as arched by the orthodontist for application to a specific patient following the procedures hereinafter described. The arch bar 12 in use is similarly arched and is used in the same manner as described hereinafter in connection with the arch bar 10. It is a feature of the invention that the spurs or fittings 96, 98, 96A, and 98A, of arch bars 10 and 12, are spaced from the arch bar respective end portions 80 and 82 to be disposed at the level of the centrums of the upper arch respective first permanent molars that they are to be disposed adjacent to, when the arch bars are arched in the manner indicated in FIG. 3 and are applied to the jaw 14 in the manners indicated in FIGS. 4, 5, and 7 (see FIG. 11), with the term "centrum" having the meaning defined hereinbefore. This is explained further hereinafter.

Referring now to FIG. 4, this Figure shows in inferior plan the arch bar 10 as applied to the upper jaw 14, and specifically the dental arch 17 of its palate 15 in the manner contemplated by said Patent. The arch bar 10 being shown in plan, its arcing that is indicated in FIG. 3 is not apparent, but in practice it is present, with the arcing in practice being substantially concentric to that of the palate 15 between the first molars 36 and 38, or transversely of the palate 15 (See FIG. 6). The arch bar 10 is employed as indicated in FIG. 4 to practice the maxillary molar derotation disclosed in said Patent as to upper arch first molars 36 and 38 the bar 10 being applied thereto from the mesial (See FIG. 9).

In preparation for application of the arch bar 10 or its equivalent arch bar 12 to the upper jaw 15, the maxillary first permanent molars 36 and 38 are each fitted with the respective conventional bands or sheathes 120 and 122 following conventional band or sheath applying practices, with each of the band or sheath members 120 and 122 being suitably equipped with lingually disposed bracket elements that are indicated by reference numerals 124 and 126, respectively, that are rigidly applied to the respective bands 120 and 122 by employing suitable bonding procedures or the like, and which are quadrilateral in transverse cross section to define through openings 125 that are of quadrilateral cross section and proportioned to resiliently receive the arch wire terminal end portions 80 and 82 in rotational movement free relation thereto, and thus to be firmly retained therein, as disclosed in said patent.

Figures 8, 9:
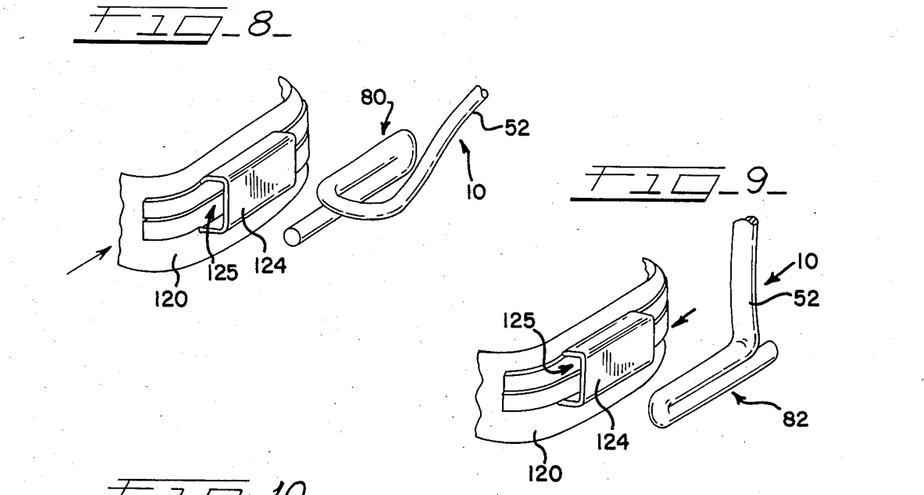
FIG. 8 is an enlarged diagrammatic perspective view, taken from a viewpoint similar to that of FIG. 6, of the molar sheath and mounting bracket thereof shown on the left hand side first permanent or anchor molar of FIG. 4 showing the arch bar terminal end portion that is applied to same, with the arch bar to have the positioning indicated by FIG. 4 (applied from the mesial)
FIG. 9 is a view similar to that of FIG. 8, but showing the arch bar as applied in the showing of FIGS. 5-7 (from the distal)

Diagrammatic FIGS. 8 and 9 diagrammatically illustrate the sheath or band 120 and its bracket element 124, both being conventional in nature, with the bracket element 124 defining through opening or chamber 125 that is open at both ends of the bracket 124, and is disposed to extend substantially mesially- distally of the arch. The band 122 and its bracket 126 are similarly arranged, but are on the opposite maxillary first molar.

The bands 120 and 122 are also equipped with conventional labially located body bracket structures 130 and 132 that are to mount the conventional labially located arch wires etc. diagrammatically illustrated in FIG. 10, as will be referred to hereinafter.

The present invention also contemplates that the maxillary canines 24 and 26 will have the respective bands or sheathes 134 and 136 applied thereto in a conventional manner. The band 134 has suitably affixed to its lingual aspect a hook member 138 having a shank 140 suitably affixed to the band 134 as at 140, following conventional dental orthodontic practices (employing silver solder bonding or the like), with the hook member 138 defining hook enc portion 142 that is gingivally directed toward the palate 15 and has the level locating positioning that will be made clear hereinafter. Similarly, the canine band or sheath 136 has hook member 144 suitably affixed to the lingual aspect of same, as at 146, and defining shank portion 148 and hook end portion 150 that has the level positioning characteristics of the hook portion 142. Hook member 144 is similarly directed to the gingival of the palate 15.

For the special purposes of this invention, the hook portions 142 and 150 are to be disposed at the level of the centrums of the respective canine teeth 24 and 26, with the term "centrum" having the meaning defined hereinbefore.

Figure 10:
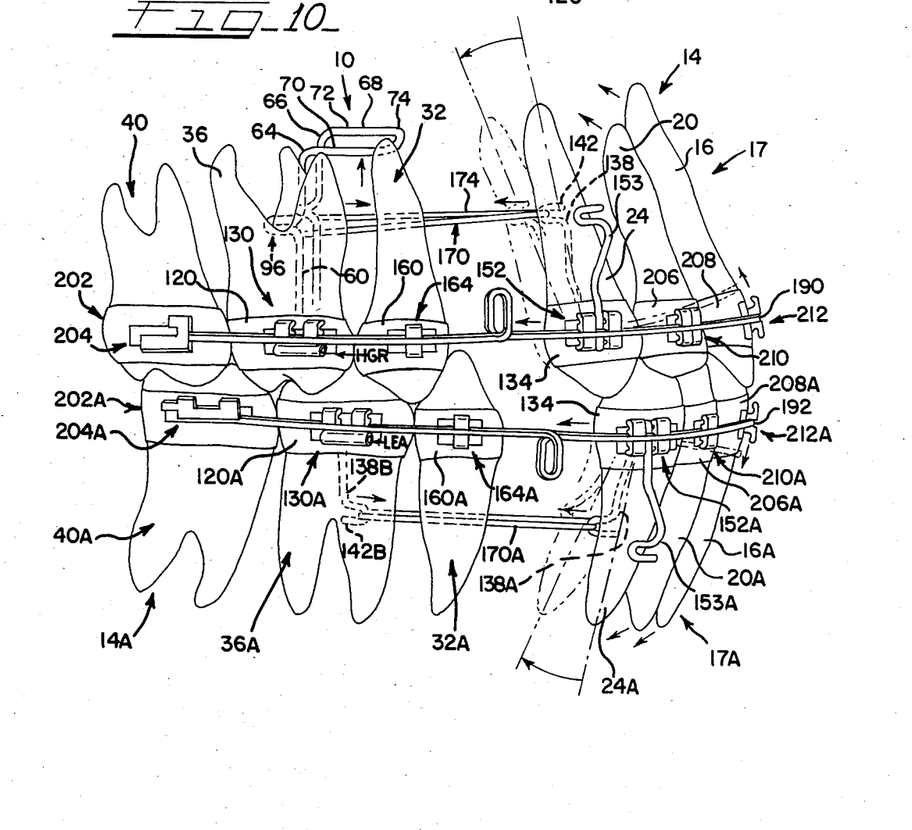
FIG. 10 is a composite diagrammatic side elevational view of the major teeth involved in the patient's upper and lower arches, taken from the right hand side of the patient's arches, illustrating the application of the invention principles thereto and also the horizontal biasing action applied to the patient's anterior teeth by employing conventional labially located arch wires at the upper and lower arches with recurved loops and which may be cinched back to activate the spring system from the labial.

The canine bands or sheathes 134 and 136 are likewise suitably equipped with the labially oriented bracket structures 152 and 154 of a conventional nature to mount the labially located arch wires etc. that are diagrammatically indicated in the showing of FIG. 10.

The second bicuspids 32 and 34, and the first bicuspids if they are left in place, of the jaw 14 are similarly equipped with the conventional sheathing or bands 160 and 162 and conventional labial bracket structures 164 and 166 for application thereto of the labially located arch wires or the like of the type illustrated in diagrammatic FIG. 10.

Assuming that the first molars 36 and 38 have been derotated, distobuccally, following the procedures of my said patent, with the arch bar 10 positioned as indicated in FIG. 4, the arch bar 10 is removed from the mesial, pivoted or turned end for end 180 degrees, so that its open loop 68 and terminal end portions 80 and 82 project toward the mesial, and its spurs 96 and 98 project toward the distal; the arch bar 10 is then reapplied to the brackets 124 and 126 from the distal, that is, the arch bar terminal end portions 80 and 82 are applied to the respective through openings 125 defined by the respective brackets 124 and 126 from the distal ends of same (see FIG. 8), whereby the positioning of the arch bar 10 is as represented in FIG. 5. Note that in this position the arch wire terminal end portions 80 and 82 are applied to the opposite brackets 124 and 126, with spurs or fittings projecting distally (this being their operative position). Assuming that the molars 76 and 78 have been derotated, distbucally, one immediate function of the arch bars 10 and 12 in the position of FIGS. 5 and 7 is to protect this positioning with the arch wires 10 and 12 disposed in the passive relation disclosed in said patent, and illustrated herein in FIGS. 5 and 7.

The next step involves application on either side of the arch 17 of the respective lingual elastics 170 and 172. The lingual elastics 170 and 172 are conventional dental elastics in the nature of rubber bands that are offerred by a number of dental appliance suppliers, such as Ortho Arch Co., of Schaumburg, Ill. Each elastic 170 and 172 comprises an endless length 174 of suitable elastomeric material well known to the art. For application of the indicated bias to the respective canines 24 and 26, the lingual elastic 170 is applied between the spur 98 of the arch bar 10, and the hook portion 142 of the hook member 138 that is bonded to the canine band or sheath 134. Similarly, the lingual elastic 172 is applied between the spur 96 of the arch bar 10 and the hook portion 150 of hook member 144 that is bonded to the sheath 136 of canine 26, resulting in the force system shown in FIG. 7, which is also diagrammatically illustrated in FIG. 11. The elastics 170 and 172 should be proportioned to apply substantially equal reciprocal forces to the arch bar spurs and canine hooks they are applied between.

Figure 6:
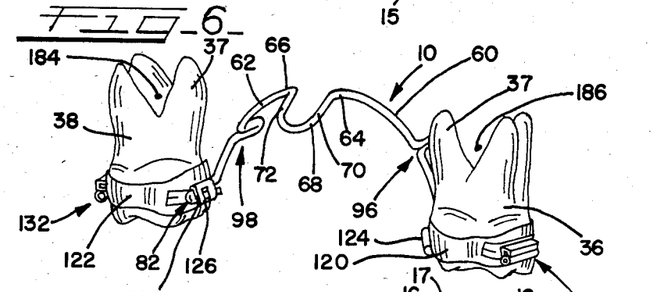
FIG. 6 is a diagrammatic perspective view of the patient's maxillary first permanent molars having the improved arch bar applied thereto in the relationship shown in FIG. 5, with the view being taken anteriorly of FIG. 5 and looking to the distal.
Figure 11:
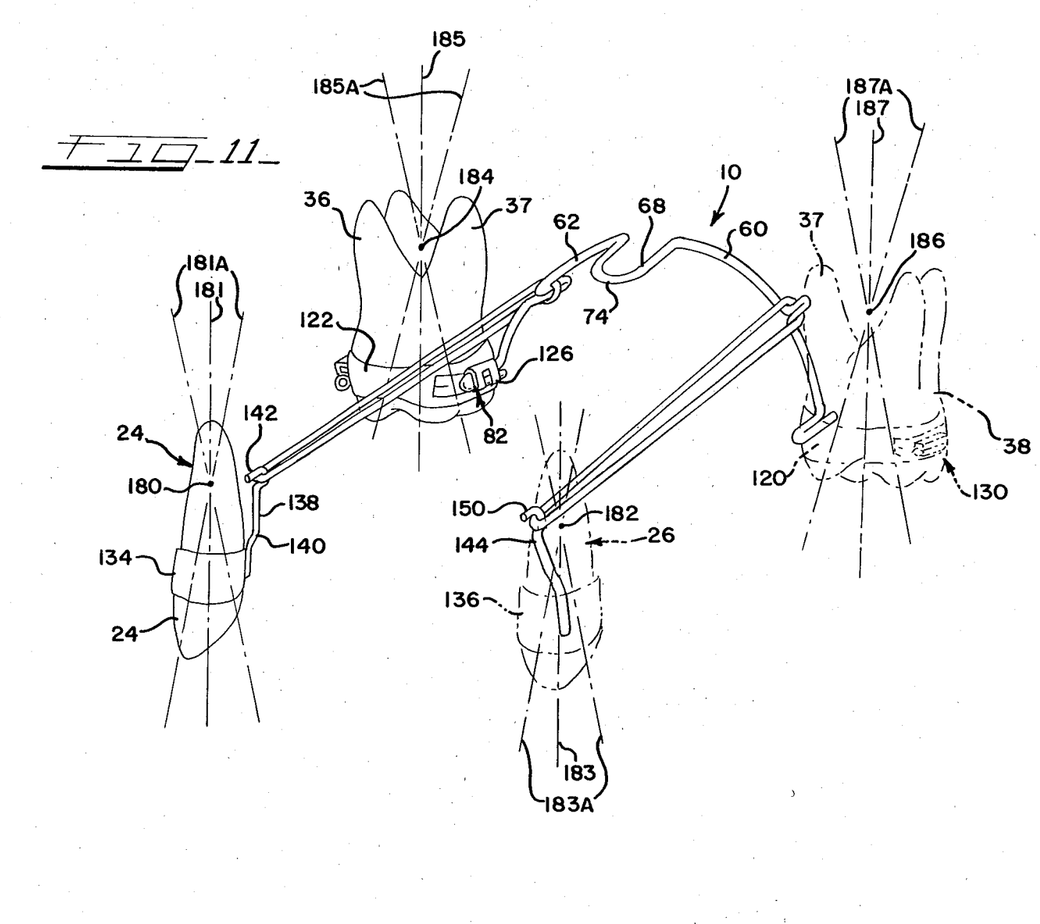
FIG. 11 is a diagrammatic perspective view similar to that of FIG. 6, but including the upper arch canines, their lingual hooks, and the lingual elastics connected therebetween and the improved arch bar, with the arch wire spurs and lingual hooks being located in accordance with an important criteria of the invention, namely, relative to the levels of centrums of the respective upper arch first permanent molars, and the permanent canine teeth.

As has been previously indicated, the forces applied to the upper arch first permanent molars and canines are reciprocal on either side of the jaw, and further, they are applied with reference to the centrums of these teeth. Referring to FIG. 11, the centrums of the upper arch canines 24 and 26 are shown at 180 and 182, respectively, while the corresponding centrums of the first molars 36 and 38 are indicated at 184 and 186, respectively. The axes of rotation of the respective canines 24 and 26 are indicated at 181 and 183, while the tipping axes of such teeth are indicated by reference numerals 181A and 183A, respectively. The corresponding rotating axes of the molars 36 and 38 are indicated by reference numerals 185 and 187, while the tipping axes of such molars are indicated by reference numerals 185A and 187A, respectively. The aforementioned palatal root of the maxillary first molars 36 and 38 is shown in FIGS. 6 and 11 at 37.

An important feature of this invention is that the ends 142 and 150 of the lingual hooks 138 and 144 to which the elastics are attached are disposed at approximately the level of the centrums 180 and 182, and the spurs 96 and 98 of the arch bar 10 are disposed, in the arched condition of the arch bar 10, and as applied to the first molars 36 and 38, at the level of the centrums 184 and 186, as already mentioned. This is diagrammatically illustrated in FIG. 11. Spurs 96A and 98A of the arch bar 12 are similarly oriented relative to the ends 80 and 82 of arch bar 12.

This application of the reciprocal forces applied by the lingual elastics 170 and 172 on either side of the upper arch 17 has the effect, as to the molars 38 and 36, to subject them to moments that tend to induce such molars to bear against the gums and related tissue holding them, for their embedded lengths from adjacent their crowns to the ends and free of tilting or tipping tendencies, and they thus become improved anchors to forces applied to the canines, whereby the resisting first molars become improved "anchor molars" in the practice of this procedure; the action of the elastics 170 and 172 on the molars 36 and 38 also effects a distobuccal rotational action on these teeth.

On the other hand, the elastics 170 and 172 apply to the canines through hook members 138 and 144 a canine root distalizing force and rotational force tending to rotate the canines distobuccally about their respective rotational axes 181 and 183 respective canine teeth are rotated about their axial centers that intersect their centrums 180 and 182, respectively, and without any substantial amount of tipping or tilting.

The result is that anchorage value of the first permanent molars is maximized while at the same time such molars are biased to rotate in the direction that tends to present their shortest crown mesial-distal diameter dimension in line with the intended dental arch of the upper jaw. Also, as to the canines, the forces delivered by the respective lingual elastics 170 and 172 a root distalizing force, and tend to rotate the canines distobuccally in a manner that tends to present their shortest crown mesial-distal diameter dimension in line with the intended dental arch of the upper jaw. In the event of overrotation of the canines disto-buccally, a conventional labial elastic may be applied between the respective canine labial brackets 152 and 154 and the respective molar labial brackets 130 and 132 for correction.

In the practice of orthodontics on the mandibular teeth of the lower dental arch, 17A, the arch bar 10 is not employed, but otherwise the same principles are employed (See FIG. 10), with the lower canines 24A being equipped with lingual hooks 138A having the same location and functioning on the lower arch canines as the upper arch canine hooks 138 and 144. The first molars 36A of the lower jaw are equipped with similar lingual hooks 138B that have their hook portion ends 142B located at the level of the centrums of the lower molars 36A (and thus have a location similar to spurs 96 and 98 of arch bar 10), and as indicated in FIG. 10, lingual elastics 170A are applied between the lower jaw canine applied hooks 138A and molar applied hooks 138B on either side of the jaw 14A.

In the showing of FIG. 10, the teeth of one side of the upper arch 17 and the lower arch 17A are shown (the right hand side of same), with the lower jaw teeth and the sheaths or bands and brackets thereof having the same reference numerals as indicated for the upper jaw teeth plus the letter "A", and the canine and molar hooks 138A and 138B, and the elastic 170A, indicating the corresponding components on both sides of the lower arch 17A.

The showing of FIG. 10 also diagrammatically illustrates the conventional application of similar sheaths or bands 202 and 202A, and the conventional labial arch end bracket 204 and 204A respectively applied thereto, to the second permanent upper and lower jaw molars 40 and 40A, and the conventional application of the respective bands or sheaths 206, 206A, and 208, 208A, and their respective conventional labial arch wire brackets 210, 210A and 212, applied thereto, to the upper and lower jaw lateral and central incisor teeth 20 and 16, respectively. Also, labial hooks 153 and 153A may be applied, on both sides of the jaws 17 and 17A to the respective canine labial brackets 130 and 132 of both jaws for use in correction of the aforementioned over rotation of the canines. This all may be done at any convenient time for use as will now be indicated, and of course, on both sides of the jaws 17 and 17A.

The upper and lower jaw canines and first permanent molars on either side of the respective jaws being equipped as indicated, the anterior teeth of the upper jaw 17 are now torqued against the lingual palate shelf, utilized with the upper jaw six anterior teeth biased against the molars and premolars by application of a horizontal moment to the upper jaw; the same type of torquing action is applied to the lower jaw anterior teeth, resulting in a similar horizontal moment being delivered to the lower jaw. For both the upper and lower jaws, the horizontal moments indicated respectively deliver approximately one half the force delivered to the canine hook portions by the respective elastics 170, 172 and 170A, and with the maximum force applied to the canines during retraction preferably not exceeding one hundred grams, this being the force relationship desired.

This, of course, may be effected in conjunction with, for instance, the conventional, labially located arch wires 190 and 192 of rectangular cross section (that are illustrated) having the usual recurved loop which is cinched back to activate the spring system involved from the labial, applied to the respective jaws, all as diagrammatically illustrated in FIG. 10. As to both the upper and lower jaws 17 and 17A, and on either side of the jaw, as the canine root of each canine is translated toward the distal, there is a gradual and continuous tipping of the mesial of the respective canine brackets toward the gingival (Note FIG. 10). With the conventional arch wires 190 and 192 tied back, and the first molars of the upper jaw given the augmented anchorage indicated through the use of the arch bar 10 (or arch bar 12), by way of the lingual elastics and the horizontally applied arch bar, or if desired, elastomeric chain, etc. there is generated a constant distalizing and torquing action to the anterior teeth of both arches.

It is also pointed out that as to the upper jaw 17, where it is desired to slip anchorage the molars 36 and 38, with the elastics 170 and 172 applied as shown in FIG. 7, the arch bars 10 and 12 may be cut on both sides short of the spurs (for instance spurs 96 and 98), and removing the thus cut away central portions of the arch bars, thereby freeing the anchor molars 36 and 38 to slip forward or mesially without the excessive mesiolingual usually seen when tying from the buccal. Under these conditions, the anterior teeth (which are being torqued against the palatal shelf) and the mass of the canine roots are now utilized as the anchorage (the six anterior teeth against the molars and premolars).

The arch bar 12 is used in the same manner as described in connection with arch bar 10.

The invention thus contemplates the arrangement and use of the improved arch bars 10 and 12 in the manner indicated, and also the improved orthodontic methods involved in using same as well as the lingual hooks and bilateral elastics that are applied in the relationships indicated on both sides of the upper and lower arches.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. In an orthodontic arch bar appliance for application to the dental upper arch of a person and between opposed molars thereof and comprising a length of spring steel wire defining a pair of spaced oppositely extending body portions integral at like ends with an open U-shaped spring loop adjacent the midportion of the bar that projects laterally of the bar and has its loop leg portions coplanar related, said wire body portions at their respective other ends being doubled over and disposed normally of the respective body portions in substantial coplanar relation to project from the wire in substantially the same direction as the loop and form the wire terminal end portions, the improvement wherein:

said wire body portions each include a spur located to be spaced from the body portion terminal end portion a distance to be disposed at the level of the centrum of the maxillary molar adjacent it when the bar is operatively applied to and between said molars, said spurs substantially paralleling said terminal end portions and projecting oppositely thereof.

2. The improvement set forth in claim 1 wherein:
said spurs are each defined by doubled over sections of the respective body portions.

3. The improvement set forth in claim 1 wherein:

said spurs each comprise a short length of metal bonded to the respective body portions.

4. The improvement set forth in claim 1 wherein: said spurs are each approximately three-four millimeters in length.

5. The improvement set forth in claim 1 wherein: the wire is arched to conform with the dental upper palatal arch in a plane that is substantially normal to said terminal end portions and said spurs.

6. An orthodontic appliance for application to the dental upper arch of a person to and between the first molars thereof and to the canine teeth thereof, said appliance comprising:

a first bracket mounted on the lingual side of one of the first molars and a second bracket mounted on the lingual side of the other first molar, said brackets each defining a quadrilaterally configured mesiodistally oriented through opening, an arch bar comprising a length of spring steel wire having a length substantially equal to the palatal distance between said brackets and shaped to define a pair of spaced oppositely extending body portions integral at like ends with an open U-shaped spring loop adjacent the midportion of the bar that projects laterally of the bar and has its loop leg portions coplanar related to lie in substantial parallelism with the upper arch palate, said wire body portions at their respective other ends being doubled over and disposed normally of the respective body portions in substantial coplanar relation to project from the wire in substantially the same direction as the loop and form the wire terminal end portions and said wire being arched and said terminal end portions being disposed for lodging in said bracket openings, said wire body portions each including a spur located to be spaced from the body portion terminal end portion a distance disposed at the level of the centrums of the maxillary first molar adjacent it when the bar is operatively applied to and between said brackets, said spurs substantially paralleling said terminal end portions and projecting distally, a first lingual hook mounted on the lingual side of one of the upper arch canine teeth, a second lingual hook mounted on the lingual side of the other of the upper arch canine teeth, said lingual hooks being located gingivally adjacent the level of the respective centrums of the maxillary canine teeth, a first lingual elastic member extending in tension between the canine hook and bar spur on one side of the arch, and a second lingual elastic member extending in tension between the canine hook and bar spur on the other side of the arch.

7. The appliance set forth in claim 6 wherein: said elastic members are in tension approximately the same amount.

8. The appliance set forth in claim 6 wherein: the tension force exerted by the respective elastic member does not exceed one hundred grams.

9. The appliance set forth in claim 6 wherein: said arch bar terminal end portions and said loop project anteriorly, said spurs projecting distally.

10. The appliance set forth in claim 9 wherein: said arch bar terminal end portions being inserted in said bracket through openings, respectively, from the distal ends of said openings.

11. The method of straightening the maxillary teeth of the human upper palatal arch including the maxillary first permanent molars and the maxillary teeth anteriorly of such first molars, which includes the steps of:

simultaneously rotating the first molars about their respective longitudinal axes to dispose the shortest mesio-distal diameter of their respective crowns in alignment with the dental arch and torquing same as needed for straightening purposes, using an arch bar connected between the lingual sides of the maxillary first molars for these purposes, removing the arch bar, equipping the lingual sides of each of the maxillary canine teeth with a gingivally directed hook located at approximately the level of the centrum of the respective maxillary canine teeth, re-establishing an arch bar connection between the maxillary first molars with a fitting located adjacent each such molar adjacent the level of the respective molar centrums, and applying a first lingual elastic between the canine tooth hook and arch bar fitting on one side of the arch and a second lingual elastic between the canine tooth hook and arch bar fitting on the other side of the arch for translation of the canine teeth.

12. The method set forth in claim 11 including: applying uniform force on the anterior teeth from the labial sides of same in the plane of the arch and acting distally to align the maxillary teeth anteriorly of the first molars in the arch and in tooth to tooth contact against the maxillary first molars.

13. The method set forth in claim 11 wherein: the arch bar that is removed is equipped to provide the fittings of said re-establishing step and said arch bar as so equipped is used to practice said re-establishing step.

14. The method set forth in claim 11 wherein: after the lingual elastics are applied by said applying steps the arch bar provided by said re-establishing step is centrally cut away short of said fittings to free said first molars for slipping mesially.

15. The method of straightening the maxillary teeth of the human upper palatal arch and the mandibular teeth of the lower arch, which method includes the steps of:

simultaneously rotating the maxillary first molars about their respective longitudinal axes to dispose the shortest mesio-distal diameter of their respective crowns in alignment with the palatal arch and torquing same as needed for straightening purposes, using an arch bar connected between the lingual sides of the maxillary first molars for these purposes, removing the arch bar, equipping the lingual sides of each of the maxillary canine teeth with a gingivally directed hook located at approximately the level of the centrum of the respective maxillary canine teeth, re-establishing an arch bar connection between the maxillary first molars with a fitting located adjacent each such molar adjacent the level of the respective maxillary molar centrums, applying a first lingual elastic between the maxillary canine tooth hook and arch bar fitting on one side of the upper arch and a second lingual elastic between the maxillary canine tooth hook and arch bar fitting on the other side of the arch for translation of the maxillary canine teeth, and applying a first lingual elastic between the mandibular canine tooth hook and the mandibular molar hook on one side of the lower arch and a second lingual elastic between the mandibular canine tooth hook and the mandibular molar hook on the other side of the lower arch for translation of the mandibular canine teeth.

16. The method set forth in claim 15 including:
applying uniform forces on the anterior teeth of both the upper and lower arches from the labial sides of same in the planes of the respective arches and acting distally to align the teeth anteriorly of the first molars in the respective arches and in tooth to tooth contact against the first molars of the respective arches.

* * * * *